United States Patent [19]

McEwan et al.

[11] Patent Number: 4,863,851

[45] Date of Patent: Sep. 5, 1989

[54] MONOCLONAL ANTIBODY TO PROSTATE SECRETORY PROTEIN

[75] Inventors: Robert N. McEwan, Richland Township, Kalamazoo County; Donald B. Carter, Kalamazoo, both of Mich.

[73] Assignee: The Upjohn Company, Kalamazoo, Mich.

[21] Appl. No.: 921,610

[22] Filed: Oct. 20, 1986

[51] Int. Cl.$^4$ .......................................... G01N 33/577
[52] U.S. Cl. .......................................... 435/7; 435/68; 435/240.27; 436/548; 436/813; 935/99; 935/100; 935/101; 935/102; 935/103; 935/104; 935/110; 530/387
[58] Field of Search ............ 435/7, 68, 240.2, 270.27; 436/548, 873; 935/99–104, 110; 530/387

[56] References Cited

U.S. PATENT DOCUMENTS 4,683,200  7/1987  Hirohashi et al. .................... 424/88
4,708,930  11/1987  Kortright et al. .................... 435/95
4,725,538  2/1988  Senger .................... 435/29

OTHER PUBLICATIONS

Frankel et al., "Monoclonal Antibodies to a Human Prostate Antigen", Cancer Research, 42 (1982) pp. 3,714–3,718.
Starling et al., "Monoclonal Antibodies to Human Prostate and Bladder Tumor Associated Antigens", Cancer Research 42 (1982) pp. 3,084–3,089.
Loor, "Characterization and Utilization of Specific Monoclonal Antibodies to Serum Market Antigens of Prostate Cancer", Hybridoma 4 (1985) 77.

Primary Examiner—Christine M. Nocker
Attorney, Agent, or Firm—Paul J. Koivuniemi; Mark DeLuca

[57] ABSTRACT

Provided are hybridomas for producing monoclonal antibodies against human prostate secretory protein (PSP15), anti-PSP15 monoclonal antibodies, fragments and derivatives thereof, and methods for their use. The antibodies are monospecific, bind to protein A and are of the IgM class of immunoglobulins. The monoclonal antibodies are useful as basic diagnostics for detecting human prostate cancer cells.

19 Claims, No Drawings

MONOCLONAL ANTIBODY TO PROSTATE SECRETORY PROTEIN

FIELD OF INVENTION

This invention relates to hybridoma technology and the production of monoclonal antibodies using that technology. More specifically, the invention relates to hybridomas that produce monoclonal antibodies directed against prostate secretory protein, the monoclonal antibodies produced thereby, and methods for using prostatesecretory protein monoclonal antibodies for diagnosing cancer cells.

BACKGROUND OF THE INVENTION

Prostate secretory protein (PSP15) is one of the major secreted proteins in human prostate fluid. Several recent studies of human prostate fluid by high resolution two-dimensional gel electrophoresis have shown PSP15 to be a 15,000 MW acidic protein having an isoelectric point of 5.5–6.0 (D. B. Carter and M. I. Resnick, The Prostate, 3, pp. 27–33 (1982); Y. C. Tsai, et al., J. Clin. Chem., 30, pp. 2026–30 (1984). PSP15 is secreted by the epithelial cells of the prostatic acini.

PSP15 appears to be the evolutionarily conserved counterpart of prostate-binding protein (PBP) described previously in the rat, dog and cynomologous and rhesus monkeys and baboons, as determined by two-dimensional gel electrophoresis and by its relative abundance in the prostatic secretion (D. B. Carter, et al., "The Antigenic Relatedness of Proteins From Human and Simian Prostate Fluid", The Prostate, 6, 395–402 (1985)). PSP15 has also been referred to as Estramustinebinding protein and prostatin. In the rat, PBP is an androgen-regulated-protein of the prostate as evidenced by the absence of expression of PBP following castration.

INFORMATION DISCLOSURE

A. H. Johnson, et al., "A Search for Differentiation Markers in Prostatic Fluid Components With Two-Dimensional Electrophoresis and Multiple Protein Detectors", The Prostate, 7, pp. 429–39 (1985) refer to components of prostatic fluid resolved by two-dimensional polyacrylamide gel electrophoresis (PAGE). They identify a component that they equate with PBP or estramustine-binding protein. Although Johnson et al. mention that monoclonal antibodies can be made to purified prostate antigenic components, they do not teach the production of the monoclonal antibodies to PSP15 of the instant invention. D. B. Carter, et al., supra., refer to purified PSP15 and to polyclonal antibodies thereto. Carter et al. do not refer to the PSP15 monoclonal antibodies of the instant invention, methods for producing them, or methods for using them in diagnosing prostate cancer cells.

T. M. Chu, et al., U.S. Pat. No. 4,446,122 refer to a prostate antigen having a molecular weight of 33,000–34,000 and an isoelectric point of 6.9, and monoclonal antibodies thereto. M. Yoshimura, et al., Great Britain patent application No. 2139645A, refer to a monoclonal antibody specific to a surface antigen of a human prostate cancer cell and a hybridoma for producing the antibody. S. Hara, et al., Japanese Early Disclosure 84-38657 refers to a prostate antigen, β-microseminoprotein, having a MW of 10,4000 and an isoelectric point of 5.6, and polyclonal antibodies thereto. None of these documents refers to PSP15, monoclonal antibodies thereto, or hybridomas and methods for producing them.

Linscott's Directory of Immunological and Biological Reagents, Third Edition, and Supplements, list two commerically available monoclonal antibodies to human prostate antigens, one against prostatic-acid phosphatase and the other to prostate specific antigen. There are no monoclonal antibodies to PSP15 cited therein.

The anti-PSP15 monoclonal antibody of the instant invention is useful as a marker in benign prostatic hyperplasia and in prostatic cancer.

SUMMARY OF THE INVENTION

The present invention relates to hybridomas producing monoclonal antibodies against prostate secretory protein (PSP15).

The present invention also relates to monoclonal antibodies to PSP15, and fragments and derivatives of the monoclonal antibodies.

The present invention also relates to methods for detecting prostate cancer cells comprising contacting monoclonal antibodies against PSP15 to human serum.

The present invention also relates to kits for detecting prostate cancer cells comprising monoclonal antibodies to PSP15.

DETAILED DESCRIPTION OF THE INVENTION

To make the hybridomas and monoclonal antibodies of the instant invention one can employ any of the techniques well known to those skilled in the art (see, for example, R. H. Kennett, et al., Monoclonal Antibodies And Functional Cell Lines (Progress and Applications), Plenum Press (1984); E. G. Engleman, et al., Human Hybridomas and Monoclonal Antibodies, Plenum Press (1985); and, Hybridomas in Biotechnology and Medicine, T. A. Springer, ed., Harvard Medical School, Dana-Farber Cancer Institute (1984) which are incorporated herein by reference). We fused spleen cells from an immune mouse with Sp2/O-Ag14 tumor cells (M. Shulman, et al., Nature, 276:269–70 (1978)) and selected for hybridomas on HAT medium. Supernatants from 480 microtiter wells were screened against prostate-fluid-coated nitrocellulose filters and positive clones were isolated. Hybridomas found to be secreting neutralizing antibody were subsequently cloned by limiting dilution and their isotypes were determined by Ouchterlony diffusion.

EXAMPLE

1. Cells and Tissue

SP2/O-Ag14 cells (M. Shulman, et al., supra.) can be obtained from The American Type Culture Collection (ATCC), by requesting deposit ATCC CRL 1581.

Human prostate tissue was obtained surgically from patients with either benign prostatic hyperplasia or prostatic carcinoma at Northwestern University Hospital.

Prostate fluid was obtained by rectal massage by a urologist and pooled before fractionation or gel electrophoresis.

2. Electrophoresis

The Laemmli SDS gel electrophoresis system was used to separate prostate fluid proteins (U. K. Laemmli, Nature, 227:680–85 (1970)). A 5% acrylamide stacking gel at pH 6.8, and a separating gel of 17% acrylamide at pH 8.8 were run at 20 ma through the stack and 100 ma through the separating gel. Western transfer of proteins to nitrocellulose sheets was performed as previously described (H. Towbin, et al., Proc. Natl. Acad. Sci. USA, 76:3149–53 (1979)). The DALT system of two-dimensional (2-D) gel electrophoresis was performed as previously described (S. Tollaksen, et al., Government Publication ANLBIM-81-1 (1981)).

3. High Pressure Liquid Chromatography

Human prostate fluid was fractionated over a Waters DEAE 5Pw column in a starting buffer of 50 mM $NH_4C_3$, pH 8.3. Proteins were eluted by a step gradient of increasing buffer concentration to a final concentration of 1M $NH_4CO_3$. Fractions were dot-blotted on nitrocellulose and then immune-reacted with polyclonal mouse anti-PSP15 followed by $^{125}I$ labelled Protein A. The PSP15 positive fractions were found repeatedly in the same peak fractions, and therefore those fractions were pooled, lyophilized, reconstituted and dialyzed against distilled water.

4. Animals and Immunizations

Four week old, female Balb/c mice (Charles River Breeding Laboratories, Inc., Wilmington MA), were injected subcutaneously with 200 μl of a 1:1 mixture of pooled, HPLC fractionated PSP15 protein (100 μg) and complete Freund's adjuvant. After two booster injections with PSP15 antigen, micer were tail bled (500 μl mouse). Blood was allowed to clot at room temperature for twenty minutes, rimmed, and incubated at 4% overnight to allow clot retraction. Sera were separated from contaminating cells and diluted 1:100 in 0.05% NP40 1X NETG (0.15M NaCl, 5.0 mM EDTA, 50 mM Tris HCl, 0.25% gelatin, pH 7.4). (H. Towbin, et al., Proc. Natl. Acad. Sci. USA, 76, pp. 4350–54 (1979)). Each animal's serum was tested against PAGE-purified PSP15 by Western analysis (Towbin, supra.). All animals were found to be positively reactive against the PSP15 protein. Three of the five animals were given booster injections three days prior to fusion of their spleen cells to the SP2/O-Ag14 cells.

5. Radioimmunoassay

Human prostate fluid was diluted 1:10 in PBS (phosphate buffered saline - 8 g/l NaCl, 0.2 g/l KCl, 0.275 g/l $KH_2PO_4$, 1.15 g/l $Na_2HPO_4$) and used to precoat nitrocellulose filters. The filters were then blocked with BSA blocking buffer as described by Towbin, et al., supra and air dried. These precoated filters were dot blotted with 150 μl of hybridoma supernatant on a Schleicher and Schuell Minifold ® filtation manifold (SRC-96/O). After five washes in 1/100×NETG/TX-100, SDS (Towbin, et al., supra), the filters were washed in $^{125}I$-labelled Protein A (New England Nuclear) $10^7$ cpm/20 ml NETG/NP40 (Towbin et al., supra). Filters were washed again as above, rinsed in $dH_2O$ and air dried. After covering with saran wrap, filters were exposed overnight to X-ray film. Positive wells were noted and cells from those wells were subcloned and their supernatants retested.

6. Fusion and Tissue Culture

Spleen cells from one mouse were fused with the murine myeloma line SP2/0-Ag14 as has been described G. Galfre and C. Milstein, "Preparation of Monoclonal Antibodies: Strategies and Procedures", Meth. Enzymol., 73, pp. 3–46 (1981). Cultures were maintained by passage in Dulbecco's Modified Eagle's Medium containing high glucose (DME, K/C Biologicals) and 20% fetal bovine serum (GIBCO), 100 μM hypoxanthine, 0.4 μM aminopterin, 16 μM thymidine, and cloned by limiting dilution as soon as possible in the same medium (I. Lefkovits and H. Waldmann, Limiting Dilution Analysis of Cells in the Immune System, Cambridge University Press, Cambridge (1979)). Cultures and clones were shifted first to medium containing 20% serum, hypoxanthine and thymidine, and then to DME containing only 10% FBS.

Isolation of antibody 4C3

The hybridomas resulting from the above fusion were screened by radioimmunoassay. This screening procedure yielded three positive cultures, 1A3, 4B2 and 4C3. Activity was maintained from 4C3 but not the other two after numerous clonings. Hybridoma 4C3 has been assigned the designation UC®HB-17 by the Upjohn Culture Depository.

Monoclonal antibody 4C3 was reactive with native prostate fluid as measured by dot blot. It was then diluted 1:100 and tested by Western blot against prostate fluid separated by PAGE and also by 2-D gel analysis. On PAGE, antibody 4C3 reacted with a single band at 15K MW and on 2-D gel it reacted with the spot originally identified as PSP15.

Of the original 480 isolates tested 475 were successful fusions. Of these fusions, 10 were initially positive in producing monoclonal antibody against PSP15. One hybridoma was cloned successfully for a final efficiency of cloning of 0.2%. Cloning was performed by the dilution cloning technique into 36 of 96 wells so that any one well contained 0.3 cells. Six single-cell-derived wells were grown up and all were tested for reactivity to PSP15 and checked for their antibody type by the Ouchterlony method (see generally, A-C Wang, "Methods of Immune Diffusion, Immunoelectrophoresis, Precipitation, and Agglutination", in J. J. Marchalonis and G. W. Warr, eds., Antibody As A Tool - The Application of Immunochemistry, John Wiley & Sons, (1982)). All of the clones were IgM's and therefore likely siblings of the original fusion.

By the same methods we have made three other hybridomas that also produce monoclonal antibodies to PSP15. These are hybridomas 7A5F9 (UC®HB-18), 8H4C7 (UC®HB-19), and 11C11B11 (UC®HB-20).

The anti-PSP15 monoclonal antibodies of the present invention can be used as diagnostics to examine androgen-dependent, prostatespecific expression of PSP15. These diagnostic assays can be applied to the urine, blood or prostatic fluid. These diagnostic assays are useful, for example, for determining the presence of metastasized prostate cells in a patient who has had his cancerous prostate removed.

To test body fluids for PSP15 using the monoclonal antibodies of the instant invention one can employ one of the following protocols:

(A) Dot-Blot Method (1) Body fluid to be tested (up to 500 μl sample; fluid sample may be concentrated to this volume) is applied to either a nitrocellulose filter or nylon membrane using a dot-blot manifold under vacuum.

(2) The filter is blocked with 10 ml of either 1.0% BSA in PBS or 0.05% Tween20 in PBS with shaking at room temperature for 1 hr.

(3) The filter is washed with PBS or BBS (borate buffered saline) 3 times at room temperature.

(4) The PSP15 monoclonal antibody diluted in NETG 0.05% NP40 (1:250–1:1000 range) is applied to the filter and incubated at room temperature for 1 hr.

(5) The filter is washed 3 times with 0.05% Tween20 in PBS.

(6) The filter is then incubated for 1 hr at room temperature with $10^7$ cpm $^{125}$I-labelled protein A in NETG 0.05% NP40, sufficient to cover th filter.

(7) The filter is washed 3 times in 0.05% Tween20 in PBS; and (8) Exposed to X-ray film with screen overnight at −80°. Alternative protocol from step 6:

(6) Incubate the filter with a second antibody (rabbit, goat or other anti-mouse antibody) diluted appropriately in BBS, for 1 hr at room temperature. The second antibody is previously conjugated to either a fluorescent substrate or some other indicator, for example, horseradish peroxidase.

(7) Wash as before.

(8) Apply the indicator sube where necessary, or examine under UV light for fluorescent probes.

(B) Dipstick Method (1) The sample is applied to either nitrocellulose or nylon filter strips by dipping the strip in the same fluid.

(2) The strip is air dried and then the same procedure is followed as for the dot blot method above.

(C) ELIZA Assay - Competition (1) Using either purified PSP15 or prostate fluid of known PSP15 content in ng, coat the wells of a 96 well ELIZA dish with the antigen and dry it. The monoclonal anti-PSP15 is then titered to react without being in excess in the well.

(2) The sample fluid and a known dilution of anti-PSP15 are incubated for 30 min at 37°. This solution is then loaded in the sample well and incubated for 1 hr at room temperature.

(3) Wells are emptied, washed 3 times with 0.05% Tween20 in PBS and then reacted with either a second antibody bound to an indicator substrate or with $^{125}$I-labelled Protein A for 1 hr at room temperature.

(4) Antibody or Protein A is washed off 3 times with 0.05% Tween20 in PBS.

(5) Indicators are added and washed, or plates are read directly by ELIZA reader or by clipping off the wells and then counting them in a gamma counter.

A part of the PSP15 monoclonal antibody of the present invention obtained by restrictive cleavage with a chemical or by enzyme treatment by well known methods (e.g., Z. Eshhar, in T. Springer, ed., supra) to produce a Fab fragment, can also be used in the methods of this invention. Such fragments are referred to herein as anti-PSP15 fragments. Anti-PSP15 fragments can also be conjugated to radionuclides or enzymes, for example, to produce derivatives thereof. The PSP15 antibodies and anti-PSP15 fragments derivatized by attachment to, for example, radionuclides, or enyzmes as set forth above, are referred to and claimed herein as "derivatives".

The hybridomas producing the monoclonal antibodies of the present invention are exemplified by hybridomas 4C3 (UC®HB-17), 7A5F9 (UC®HB-18), 8H4C7 (UC®HB-19), and 11C11B11 (UC®HB-20). Hybridoma 4C3 was deposited at the American Type Culture Collection, Rockville MD, (ATCC) on 10 June 1986, and is available therefrom by requesting deposit number ATCC HB 9121. Hybridomas 7A5F9, 8H4C7, and 11C11B11 were also deposited at the ATCC on 7 October 1986, and are available therefrom by requesting deposit numbers ATCC HB 9224, ATCC HB9225, and ATCC HB 9226 respectively.

We claim:

1. A hybridoma which produces monoclonal antibodies against human prostate secretory protein PSP15.

2. A hybridoma according to claim 1, selected from the group consisting of ATCC HB 9121, ATCC HB 9224, ATCC HB9225, and ATCC HB 9226.

3. An imunoglobulin molecule selected from the group consisting of monoclonal antibodies to human prostate secretory protein PSP15, anti-PSP15 fragments, derivatives of monoclonal antibodies to PSP15, and derivatives of anti-PSP15 fragments.

4. An antibody according to claim 3 which is a monoclonal antibody to PSP15.

5. An anti-PSP15 fragment according to claim 3 produced by restrictive chemical cleavage or enzymatic digestion.

6. An anti-PSP15 fragment according to claim 5 which is Fab.

7. A monoclonal antibody according to claim 3, produced by a hybridoma selected from the group consisting of ATCC HB 9121, ATCC HB 9224, ATCC HB9225, and ATCC HB 9226.

8. Derivatives of monoclonal antibodies to PSP15 according to claim 3 which are monoclonal antibodies to PSP15 labeled with radioactive material.

9. Derivatives of anti-PSP15 fragments according to claim 3 which are monoclonal anti-PSP15 fragments labeled with radioactive material.

10. A method of detecting human prostate cancer cells comprising the steps of:
(a) contacting monoclonal antibodies against human PSP15 and fragments and derivatives thereof to human fluids;
(b) maintaining said monoclonal antibodies in contact with said human fluids for a time and under conditions sufficient for the formation of immunological complexes between said monoclonal antibodies and PSP15 molecules present in said human fluids; and
(c) detecting said immunological complexes resulting.

11. A method according to claim 10 wherein the monoclonal antibody against human PSP15 is produced by a hybridoma selected from the group consisting of ATCC HB 9121, ATCC HB 9224, ATCC HB9225, and ATCC HB 9226.

12. A method according to claim 10 wherein:
(a) prior to contacting said monoclonal antibodies to said human fluids, said human fluids are applied to a substrate member under conditions which allow said human fluid to bind to said substrate;
(b) said bound human fluids are then contacted with said monoclonal antibodies;
(c) contact of said monoclonal antibodies with said bound human fluids is maintained for a time and under conditions sufficient to allow formation of a first immunological complex; and
(d) said first immunological complex is then detected by washing off monoclonal antibodies not immunologically complexed with said human fluid bound to said substrate, said first immunological complex is then contacted with a second antibody which is specific against said monoclonal antibody to allow formation of a second immunological complex of said second antibody with said first immunological complex, said second antibody having attached to it an indicator which can be detected 13. A method according to claim 12 wherein said indicator attached to said second antibody is a radioactive substance which can be detected and measured.

14. A method according to claim 12 wherein said indicator attached to said second antibody is a fluorescent substance which can be detected and measured.

15. A method according to claim 12 comprising the additional step of measuring the quantity of said immunological complexes.

16. A method according to claim 10 comprising the additional step of measuring the quantity of said immunological complexes.

17. A method according to claim 16 wherein:
(a) a known quantity of said monoclonal antibodies is contacted with said human fluids;
(b) contact of said monoclonal antibodies with said human fluids is maintained for a sufficient time to allow for said formation of immunological complexes;
(c) said immunological complexes are then detected and measured by contacting said monoclonal antibodies and human fluids mixture with a substrate that has been coated with a known quantity of PSP15 to allow formation of immunological complexes of uncomplexed monoclonal antibodies with said PSP15 that is attached to said substrate, said substrate is then washed to remove remaining uncomplexed monoclonal antibodies and a second antibody is contacted with said washed substrate, said second antibody is attached to an indicator and is specific against said monoclonal antibodies to allow formation of immunological complexes of said second antibody with monoclonal antibodies complexed with PSP15 attached to sadi substrate, said substrate is washed to remove any second antibody not complexed with said monoclonal antibody/PSP15 complex, the amount of indicator is measured to determine the amount of said second antibody complexed with said monoclonal antibodies, and the amount of PSP15 in said body fluid.

18. A method according to claim 17 wherein said indicator attached to said second antibody is a radioactive substance which can be detected and measured.

19. A method according to claim 17 wherein said indicator attached to said second antibody is a fluorescent substance which can be detected and measured.

* * * * *